US008269825B1

(12) United States Patent
Vu et al.

(10) Patent No.: US 8,269,825 B1
(45) Date of Patent: Sep. 18, 2012

(54) VIDEO OBSERVATION OF A PATIENT'S FACE DURING A MEDICAL PROCEDURE WHILE THE PATIENT IS IN A PRONE POSITION

(75) Inventors: An Binh Vu, Carlsbad, CA (US); Gregory Philip Jordan, Carlsbad, CA (US)

(73) Assignee: Dupaco, Inc., Oceanside, CA (US)

( * ) Notice: Subject to any disclaimer, the term of this patent is extended or adjusted under 35 U.S.C. 154(b) by 586 days.

(21) Appl. No.: 12/506,809

(22) Filed: Jul. 21, 2009

Related U.S. Application Data

(63) Continuation-in-part of application No. 11/867,242, filed on Oct. 4, 2007.

(51) Int. Cl.
*H04N 7/18* (2006.01)
(52) U.S. Cl. .......................................................... 348/77
(58) Field of Classification Search ...................... 348/77
See application file for complete search history.

(56) References Cited

U.S. PATENT DOCUMENTS

| | | | |
|---|---|---|---|
| 4,752,064 A * | 6/1988 | Voss .................................. | 5/638 |
| 5,220,699 A | 6/1993 | Farris | |
| 5,406,327 A * | 4/1995 | Guarnotta ..................... | 348/143 |
| 5,443,058 A | 8/1995 | Ough | |
| 6,081,606 A * | 6/2000 | Hansen et al. ................ | 382/107 |
| 6,490,737 B1 | 12/2002 | Mazzei et al. | |
| 6,621,917 B1 * | 9/2003 | Vilser ........................... | 382/128 |
| 7,165,860 B1 | 1/2007 | Metzger | |
| 2004/0015191 A1 | 1/2004 | Otman et al. | |
| 2005/0066444 A1 | 3/2005 | Mazzei | |
| 2005/0267328 A1 * | 12/2005 | Blumzvig et al. ............ | 600/109 |
| 2007/0132597 A1 * | 6/2007 | Rodgers ..................... | 340/573.1 |
| 2008/0117328 A1 * | 5/2008 | Daoud et al. ................. | 348/373 |
| 2008/0262312 A1 * | 10/2008 | Carroll et al. ................ | 600/160 |
| 2009/0321593 A1 * | 12/2009 | Foddis ........................ | 248/187.1 |

OTHER PUBLICATIONS

Grant, et al., "Use of the Proneview Helmet System with a Modified Table Platform for Open Access to the Eyes During Prone Spine Surgery". Anesthesia &Analgesia, vol. 103, No. 2, Aug. 2006, pp. 499-500.

* cited by examiner

*Primary Examiner* — Firmin Backer
*Assistant Examiner* — Jonathan Bui
(74) *Attorney, Agent, or Firm* — Edward W. Callan

(57) ABSTRACT

Apparatus that allows at least one feature of a patient's face to be observed while the patient is in a prone position includes a facial cushion, a video camera and a monitor. A self supporting facial cushion provides cranial support for a patient in a prone position during a medical procedure. The cushion has a frontal aperture that is dimensioned so that the facial feature of a patient wearing the facial cushion and in a prone position are visible through the at least one aperture. A portion of the facial cushion that contacts a supporting surface when the facial cushion is self supported defines a tunnel through which at least the lens of the video camera can be inserted for movement from outside the facial cushion to a position beneath the patient's face.

10 Claims, 6 Drawing Sheets

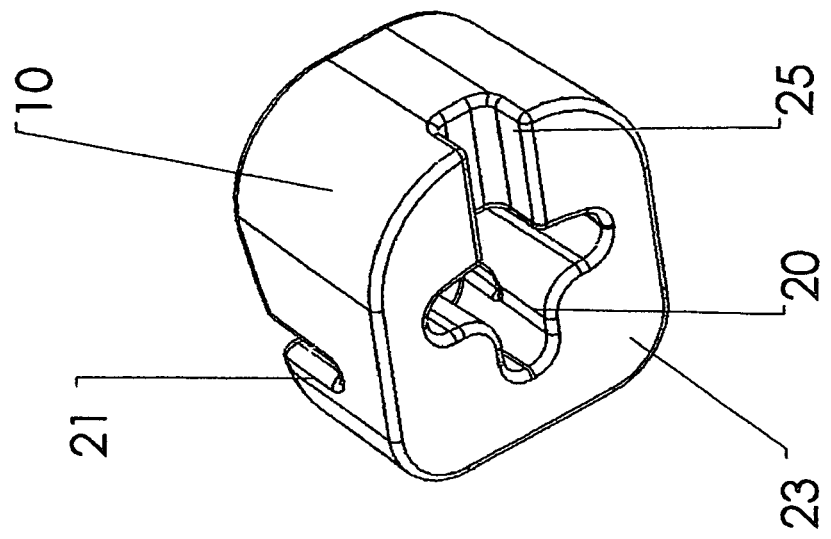
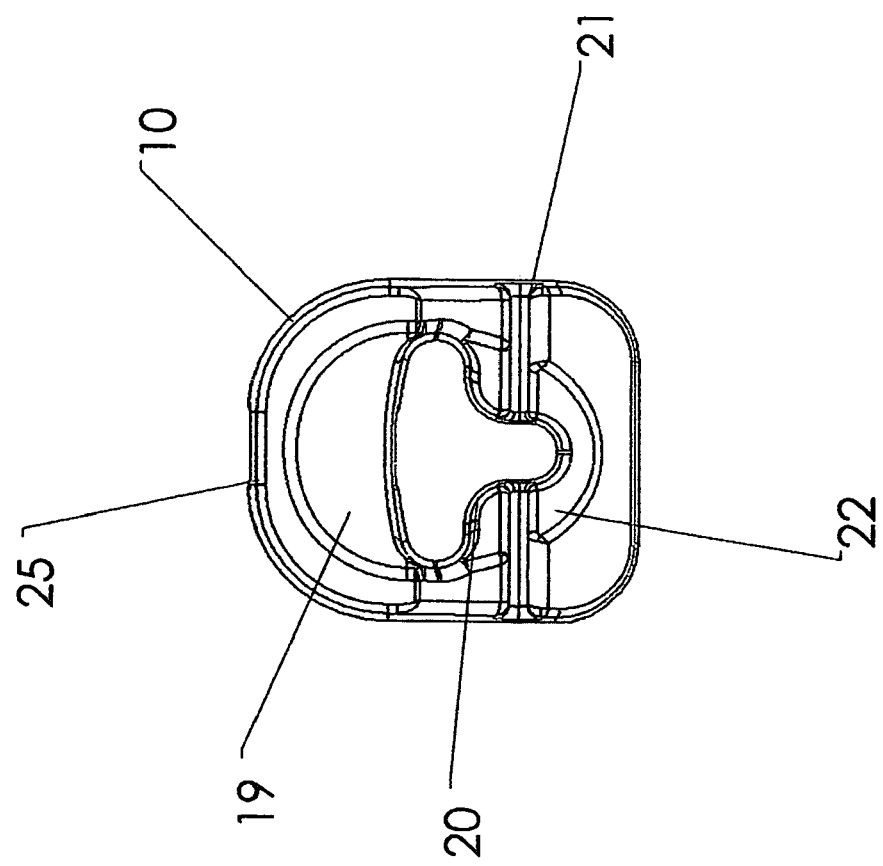

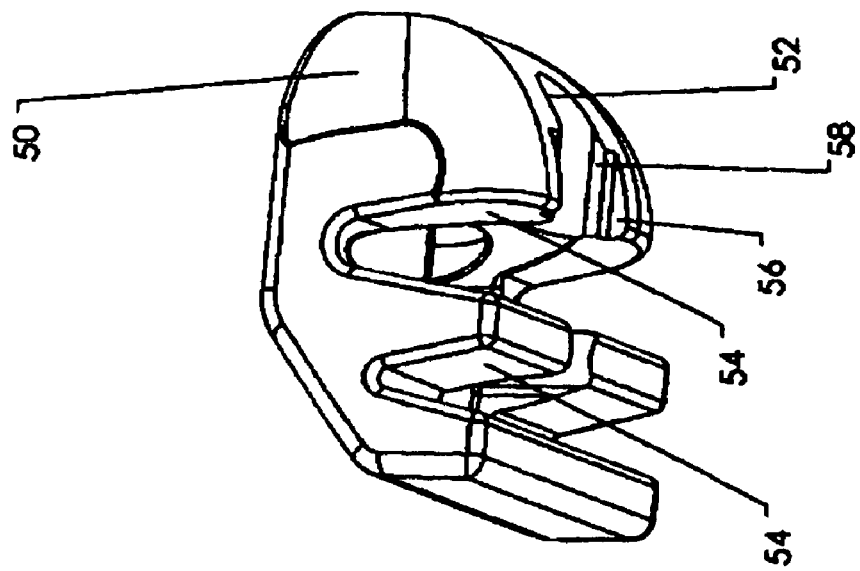
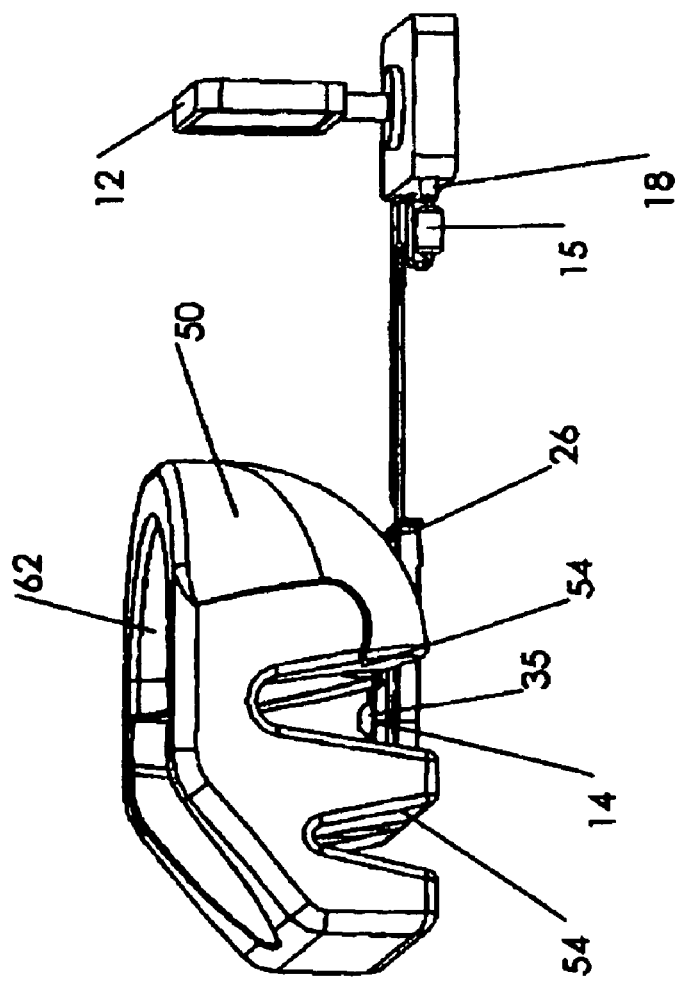

VIDEO OBSERVATION OF A PATIENT'S FACE DURING A MEDICAL PROCEDURE WHILE THE PATIENT IS IN A PRONE POSITION

CROSS REFERENCE TO RELATED APPLICATION

This is a continuation-in-part of co-pending application Ser. No. 11/867,242 filed Oct. 4, 2007.

BACKGROUND OF THE INVENTION

The present invention generally pertains to medical apparatus and is particularly directed to apparatus that allows various features of a patient's face, such as the eyes, nose and/or mouth, to be observed while the patient is in a prone position.

Such an apparatus is described in U.S. Pat. No. 4,635,625 to William Mazzei, Gregory Jordan and An Vu. The apparatus includes a facial cushion for providing cranial support for a patient during surgery. The facial cushion is dimensioned for achieving optimum fit and pressure diffusion upon the face of the patient. The facial cushion has a frontal aperture and viewing passages in the cushion sidewalls. The aperture and the viewing passages are so dimensioned and relatively disposed that the eyes, nose and mouth of a patient in the prone position and wearing the facial cushion may be seen through the viewing passages from positions adjacent to the sidewall viewing passages. In one embodiment, the apparatus further includes a mirrored surface, which is disposed beneath the cushion to enable upright individuals standing adjacent to the facial cushion to view images of the features of the patient's face that are visible through the aperture and reflected off of the mirrored surface.

SUMMARY OF THE INVENTION

The present invention provides apparatus that allows at least one feature of a patient's face to be observed while the patient is in a prone position, comprising: a facial cushion for providing cranial support for a patient in a prone position during a medical procedure, wherein the cushion has at least one frontal aperture that is dimensioned so that at least one facial feature of a patient wearing the facial cushion and in a prone position is visible through the at least one aperture from beneath the patient; and a video camera having a lens for providing video signals representing images of the at least one facial feature that is visible through the at least one frontal aperture when the cushion is supporting the head of a patient in a prone position; wherein a portion of the cushion defines a tunnel through which at least the lens of the video camera can be inserted longitudinally with respect to a patient's face from outside the cushion to a position that is beneath the patient's face when a patient wearing the facial cushion is in the prone position.

The present invention facilitates the insertion of the video camera to a position beneath the patient's face after the patient wearing the facial cushion has been placed in a prone position.

The present invention enhances the ability of medical personnel, such as anesthesiologists and anesthetists, to meet a requirement of periodically recording in a surgical procedure file that they checked the patient's eyes every specified interval, typically every fifteen minutes, to ensure that no pressure from the facial cushion or any other material is impacting the patient's eyes. It becomes more difficult and inconvenient to periodically view the patient's facial features at the required times as the medical procedure becomes longer and longer. Some medical procedures in which the patient is in a prone position take at least ten hours. The present invention allows medical personnel to view the patient's facial features by looking at a video monitor, instead of stooping, looking in a mirror or having to get out of a chair to look around the patient's head to see that the patient's eyes are safely within the frontal aperture of the facial cushion with nothing touching them. The present invention also obviates the necessity of the medical personnel having to engage in a dangerous practice of poking around the patient's eyes with their fingers in order to make the periodically required observations.

Additional features of the present invention are described with reference to the detailed description of the preferred embodiments.

BRIEF DESCRIPTION OF THE DRAWING

FIG. 2 is a top plan view of the facial cushion included in the embodiment shown in FIG. 1.

FIG. 3 is a perspective view of the facial cushion included in the embodiment shown in FIG. 1, as viewed from beneath and to one side of the cushion.

FIG. 7 is a perspective view of another embodiment of an apparatus according to the invention.

FIG. 8 is a perspective view of the facial cushion included in the embodiment shown in FIG. 7.

DETAILED DESCRIPTION

Figure 1:
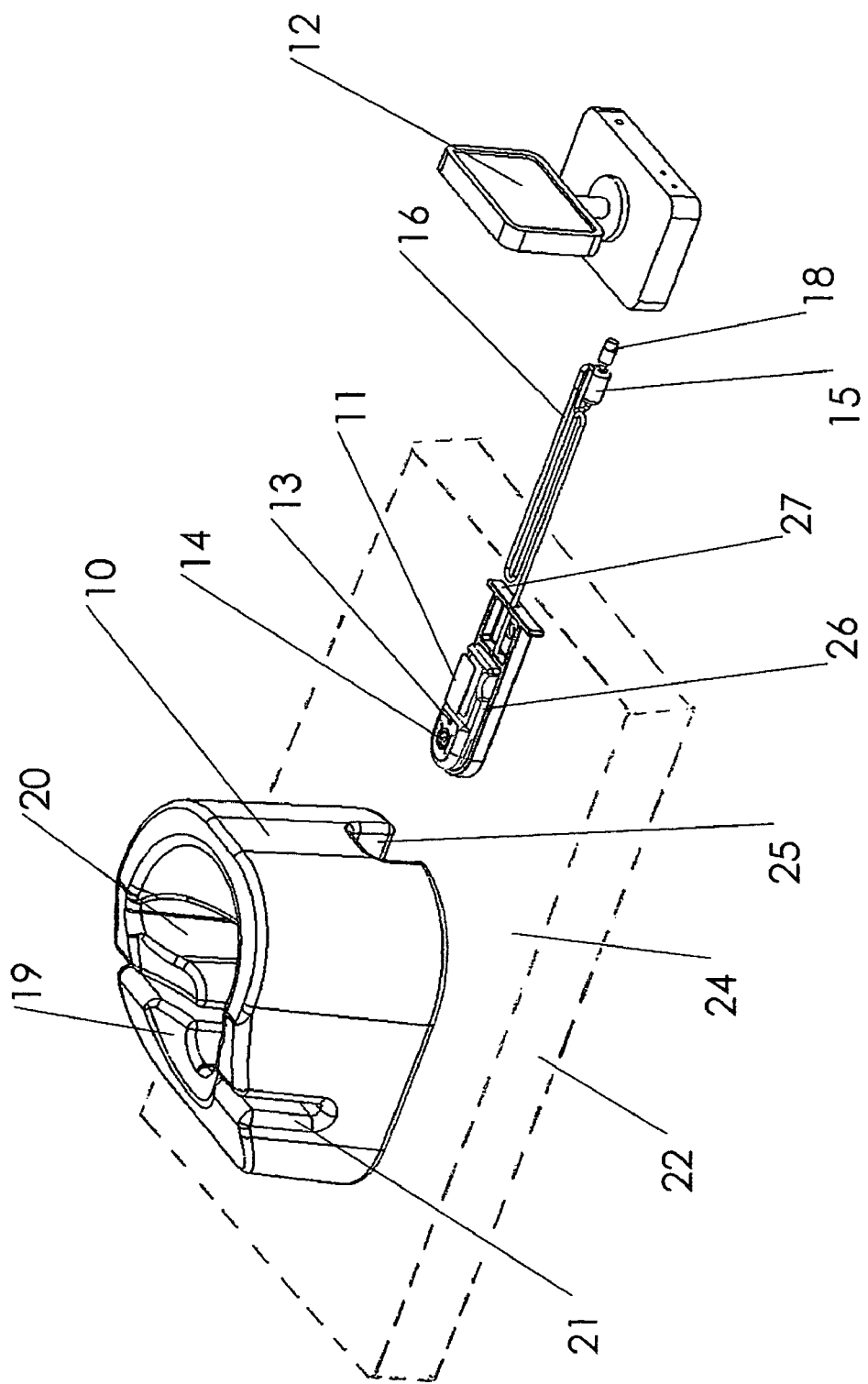
FIG. 1 is a perspective view of one embodiment of an apparatus according to the invention.
Figure 4:
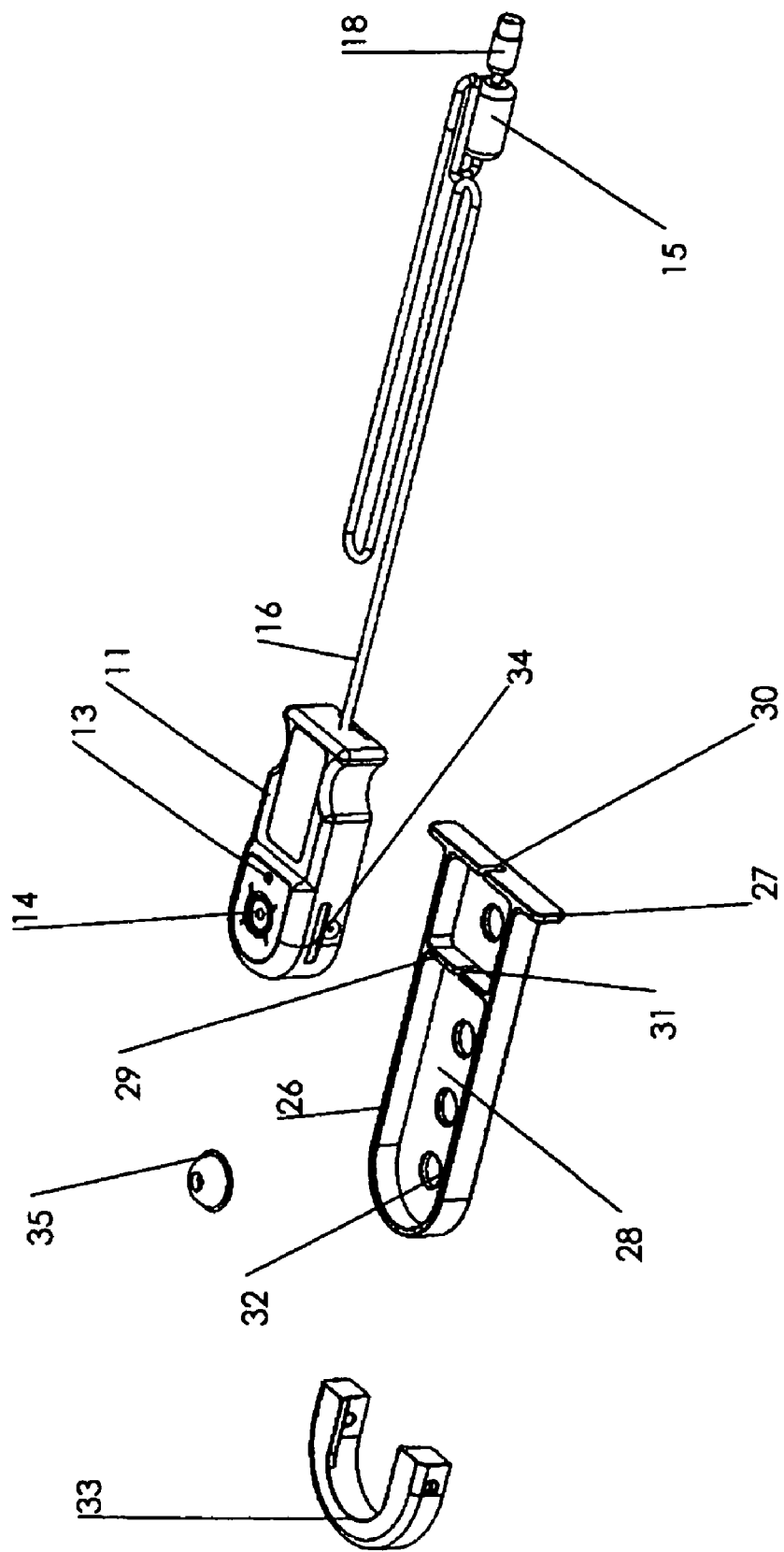
FIG. 4 is an exploded perspective view of the video camera and the tray included in the embodiment shown in FIG. 1, together with a receptacle and a transparent dome.

Referring to FIGS. 1, 2 3 and 4, one embodiment of an apparatus according to the present invention includes a facial cushion 10, a video camera 11 and a video monitor 12. The video camera 11 is embedded in a cartridge which includes a light source 13. The video camera 11 includes a lens 14 embedded in the cartridge and a video circuit box 15, which is connected to the video lens 14 by a cable 16. The video circuit box 15 is connected to the video monitor 12 by a connector 18. In some embodiments the video circuit box 15 is also embedded in the cartridge. The video camera 11 may be powered by a rechargeable battery (not shown) or otherwise, such as via a line from a wall socket.

The light source 13, such as an LED or an infrared source, is attached to the video camera 11 adjacent to the camera lens 14 to enhance the clarity of the images provided by the video camera 11. When the setting has relatively low ambient lighting, a video camera 11 having a low lux rating may be used either, in combination with, or instead of the light source 13.

In the preferred embodiments, the video camera 11 is an audio-video camera that includes a microphone (not shown), and provides color images. In alternative embodiments, a microphone is not included in the video camera 11 and/or the video camera 11 provides monochromatic images.

The facial cushion 10 provides cranial support for a patient in a prone position during a medical procedure. The interior surface 19 of the facial cushion 10 is dimensioned for achieving optimum fit and pressure diffusion upon the face of the patient.

The facial cushion 10 has a frontal aperture 20. The frontal aperture 20 is dimensioned so that the eyes, nose and mouth of a patient wearing the facial cushion 10 and in a prone position are visible through the frontal aperture 20 from beneath the patient. Slots 21 are provided in sidewalls of the facial cushion 10 for guiding an endotracheal tube (not shown).

The facial cushion 10 is one piece. In an alternative embodiment (not shown) the facial cushion has a plurality of pieces.

The facial cushion 10 is self-supporting and configured for mounting on a platform 22. The platform 22 may be a table, such as an operating table. In some embodiments, the platform 22 can be attached to and off the end of any operating table or to and off the sides or on the rails of an operating table.

The bottom portion 23 of the facial cushion 10 that contacts a supporting surface 24 of the platform 22 when the facial cushion 10 is self supported defines a tunnel 25 through which the video camera 11 can be inserted for movement from outside the facial cushion 10 to a position beneath the patient's face while a patient wearing the facial cushion 10 is in the prone position.

The video camera 11 may be placed in a tray 26 that is dimensioned for carrying the video camera 11 through the tunnel 25 in the facial cushion 10. The tray 26 includes a bar 27 having a lateral dimension that is wider than the width of the tunnel 25. The bar 27 is disposed on the tray 26 for limiting the distance of movement of the tray 26 through the tunnel 25 so that in accordance with the length of the tray 26 and the configuration of the cushion 10, the lens 14 of the video camera 11 within the tray 26 can be located in a predetermined stationary position beneath the face of a patient wearing the facial cushion 10.

The tray 26 includes a compartment 28 that is dimensioned by moving a slideable interior wall 29 for fitting the video camera 11 within the compartment 28 so that the video camera 11 does not slide and change position with respect to the tray 26 when the video camera 11 is placed in the compartment 28 of the tray 26. The bar 27 on the tray 26 and the interior wall 29 of the tray 26 respectively contain slots 30, 31 for guiding the passage of the cable 16 from the video camera 11.

The bottom of the tray 26 includes a plurality of holes 32 for draining fluid from the tray 26 when fluid collects within the tray 26 during the course of a surgical procedure.

A receptacle 33 is provided for placement beneath the frontal aperture 20 of the cushion 10 when the facial cushion 10 is self supported on the platform 22. The receptacle 33 is disposed on the platform 22 and is adapted for enabling the lens 14 of the video camera 11 to be located in a predetermined stationary position beneath the face of a patient wearing the facial cushion 10 when the tray 26 is inserted through the tunnel 25 in the cushion 10.

In some alternative embodiments (not shown), either only the bar 27 or the receptacle 33 is included.

The cartridge of the video camera 11 includes guide slots 34 for engaging the receptacle 33 to facilitate placement of the video camera 11 in the predetermined position when the tray 26 is inserted through the tunnel 25 in the facial cushion 10.

A transparent dome 35 is provided for covering the lens 14 of the video camera 11 in order to shield the lens 14 from fluids secreted by a patient wearing the facial cushion 10 and in the prone position above the lens 14.

The video camera lens 14 is disposed beneath the facial cushion 10 for providing a sequence of video signals representing sequential images of the facial features that are visible through the frontal aperture 20. In various alternative embodiments, the sequence of video signals represent relatively continuous images or time-lapsed images, such as images at five-minute intervals, as determined by a timer in the video camera circuit box 15.

In the preferred embodiments, the camera lens 14 is a wide angle lens for providing a relatively undistorted image of at least the portion of the patient's face that extends laterally to fully include both eyes. A preferred wide angle lens is a 1.9 mm super wide angle lens having a focal length of at least one inch.

The video monitor 12 is coupled to the video camera 11 by either a cable or a wireless interface for enabling the images of the visible facial features represented by the video signals provided by the video camera 11 to be monitored in real time. Preferably, the video monitor 12 is located so that it can be viewed by medical personnel having the responsibility of observing the various features of the patient's face during the medical procedure in order to detect any change in such features that could be detrimental to the patient, such as a movement of the patient's face relative to the facial cushion 10 that causes any part of the eyes to be impacted by the facial cushion 10 or some other device in the proximity. A person, typically an anesthetist or an anesthesiologist, views the video monitor 12 at least periodically during the course of the medical procedure and makes a periodic record of the status of the facial features observed on the video monitor 12.

In addition to monitoring a patient's eyes, the patient's mouth and/or nose are also monitored by use of the video monitor 12 to make sure that the patient's air passages are not obstructed and/or that tubing inserted into the patient's air passages have not been removed therefrom and/or that such tubing has not become disconnected from a breathing circuit.

Figure 5:
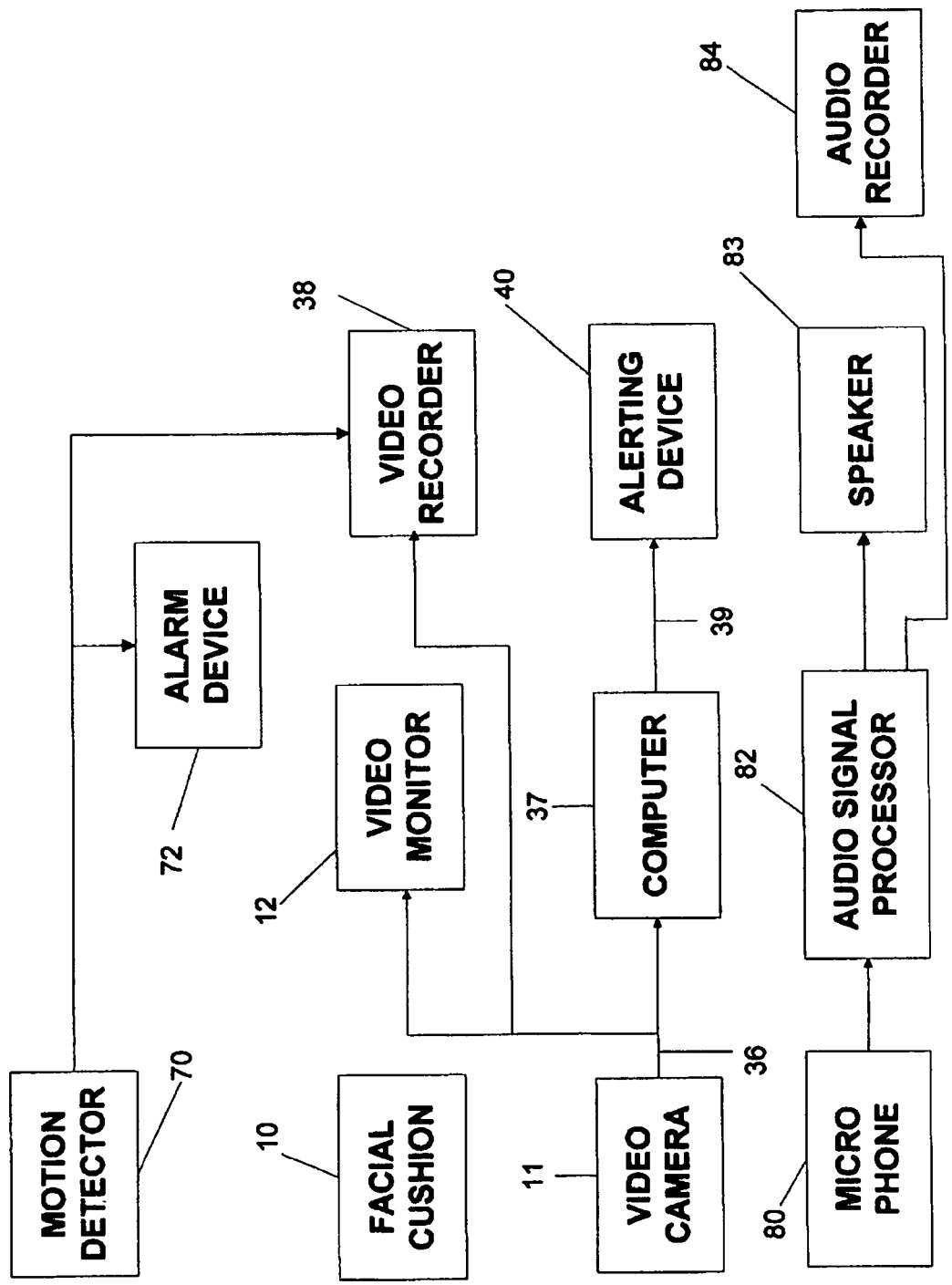
FIG. 5 is a block diagram of an embodiment of the invention in which a video monitor, a computer and a video recorder are coupled to the video camera.

Referring to FIG. 5, in various alternative embodiments, video signals 36 representing sequential images of the facial features observed from beneath the facial cushion 10 are provided by a video camera 11 disposed beneath the facial cushion 10 to a video monitor 12, a computer 37 and/or a video recorder 38. The video monitor 12, the computer 37 and the video recorder 38 are respectively coupled to the video camera 11 by a wireless interface or by a hardwired connection.

The computer 37 is programmed for processing the video signals to detect a change in at least one aspect of the sequential images that exceeds a predetermined threshold and, when the predetermined threshold is exceeded, to provide a signal 39 to a device 40 that alerts the medical personnel to such a detected change.

Figure 6:
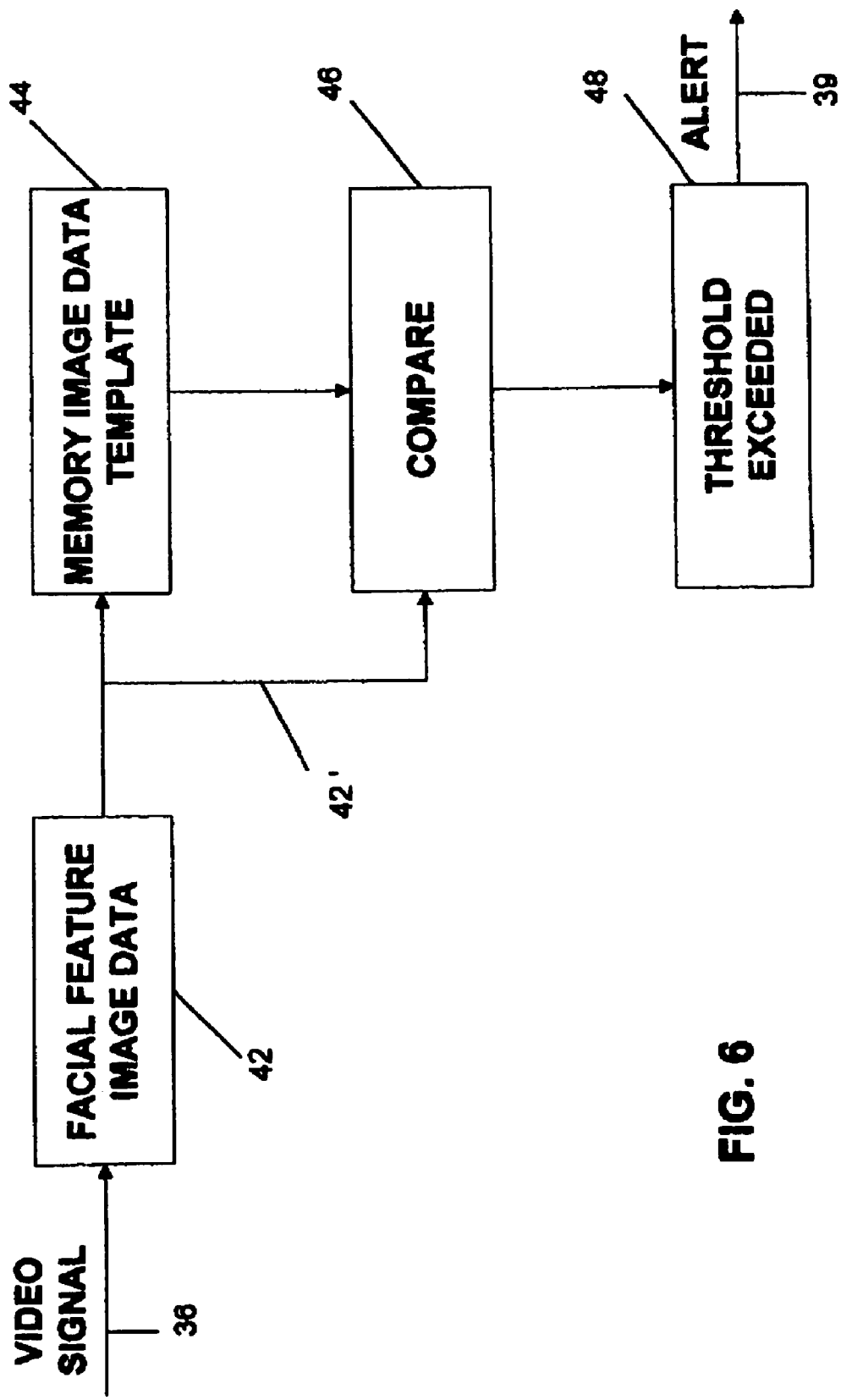
FIG. 6 is a block diagram of an embodiment of signal processing by the computer included in the embodiment shown in FIG. 5.

Referring also to FIG. 6, the video signals 36 are processed by the computer 37 to provide facial-feature-image data 42. The initial facial-feature-image data 42 is stored as an image data template in a memory 44 of the computer 37. The computer 37 performs a routine 46 of comparing the stored image data template in the memory 44 to facial-feature-image data 42' provided by processing the subsequent sequential video signals 36 from the video camera 11 in order to detect a change in at least one aspect of the sequential images that exceeds the predetermined threshold. Facial recognition software may used to implement this feature.

Whenever the predetermined threshold is exceeded, as shown at 48, the computer 37 provides the signal 39 to the device 40 that alerts a person to such a detected change. The alert is of an audible, visual and/or vibratory nature. The alert is provided to the person having the responsibility of observing the various features of the patient's face during the medical procedure. After an alert has been provided and the patient's face is once again placed in a desired position relative to the facial cushion 10, the image data template that is stored in the memory 44 is once again initialized.

The video recorder 38 records the video signals provided by the video camera 11 to provide a record of the sequential images of the visible facial features over the duration of the medical procedure in which the patient is wearing the facial cushion and in a prone position. The recorded images may be time-lapsed images to limit the amount of memory required to preserve the record of the sequential images. The recorded images may be used to corroborate the records made by a person viewing the video monitor 12 during the course of the medical procedure. The recorded images may be downloaded from the video recorder 38 to a portable data storage device, such as disc or a memory stick, that can be put into the patient's file.

Referring to FIGS. 7 and 8, a further embodiment of the apparatus of the present invention includes a facial cushion 50 that is self-supporting and configured for mounting on a platform (not shown), such as the platform 22 described above. The facial cushion 50 has a frontal aperture 52, which includes viewing passages 54 in the cushion sidewalls. The viewing passages 54 are formed by extension of the frontal aperture 52 into the cushion sidewalls.

In an alternative embodiment (not shown) the frontal aperture and the viewing passages are separated by a portion of the cushion sidewall rather than being formed by an extension of the frontal aperture 52, as shown in FIGS. 7 and 8.

One of the bottom portions 56 of the facial cushion 50 that contacts a supporting surface of a platform (not shown) when the facial cushion 50 is self supported defines a tunnel 58 in a portion of the frontal aperture 52. The lens 14 of a video camera can be inserted through the tunnel 58 for movement from outside the facial cushion 50 to a position beneath the patient's face while a patient wearing the facial cushion 50 is in the prone position.

The camera lens 14 is held in the stationary position by a lens holder 60. The lens holder 60 is slid through the tunnel 58 and into a receptacle, such as the receptacle 33 described above, so that the lens 14 and the facial cushion 50 are held in a stationary relationship to one another. The receptacle is disposed on the platform for locating the camera lens 14 in a stationary position beneath the facial cushion 50.

The lens 14 is covered by a transparent dome, such as the transparent dome 35 described above, for shielding the lens 14 from fluids secreted by a patient wearing the facial cushion 50 and in the prone position above the lens 14.

In an alternative embodiment, a video camera, such as the video camera 11 described above, may be placed in a tray, such as the tray 26 described above, for movement through the tunnel 58 in the facial cushion 50.

The facial cushion 50 provides cranial support for a patient in a prone position during a medical procedure. The interior surface 62 of the facial cushion 50 is dimensioned for achieving optimum fit and pressure diffusion upon the face of the patient.

The frontal aperture 52 is dimensioned so that the eyes, nose and mouth of a patient wearing the facial cushion 50 and in a prone position are visible through the frontal aperture 52 from beneath the patient. The viewing passages 54 of the frontal aperture 52 are so dimensioned and disposed that the eyes, nose and mouth of a patient in the prone position and wearing the facial cushion may be seen through the viewing passages 54 from positions adjacent to the sidewall viewing passages 54. The facial cushion 50 is made of one component.

In an alternative embodiment (not shown) the facial cushion is made of a plurality of components.

In some embodiments, the platform has a mirrored upper surface. The mirrored surface is disposed beneath the facial cushion 50 to enable upright individuals standing adjacent to the facial cushion 50 to view images of the features of the patient's face that are reflected off of the mirrored surface. The receptacle holds the video camera lens 14 in a stationary position on the mirrored surface. This mirrored surface feature provides an additional way to observe the facial features of the patient in the event that for some reason the display of the facial features on the video monitor 12 is interrupted.

Referring again to FIG. 5, in some embodiments a motion detector 70 is located on the platform within the frontal aperture of the facial cushion 10 beneath the patient's face for detecting any movement in the field of view of the motion detector 70, such as movement by at least one of the various features of the patient's face during the medical procedure or movement by a device in the vicinity of at least one of such features of the patient's face. An alarm device 72 is coupled to the motion detector 70 for alerting medical personnel when the motion detector 70 detects such movement so that an immediate investigation can be conducted to determine whether the detected movement was correlated with any change in such features that could be detrimental to the patient, such as a movement of the patient's face relative to the facial cushion 10 that causes any part of the eyes to be impacted by the facial cushion 10 or movement by a device in the vicinity of such features of the patient's face.

The video recorder 38 is coupled to the motion detector 70 and is adapted to begin recording the video signals 36 from the video camera 11 whenever the motion detector 70 detects movement by any of such features of the patient's face or movement by a device in the vicinity of such features of the patient's face. Accordingly, a documentary record is provided in the event of detection of any such detected movement.

Still referring to FIG. 5, the apparatus of the present invention may be used in combination with an audio system for allowing the breathing of a patient to be monitored while the patient is wearing the facial cushion and in the prone position. The audio system includes a microphone 80, an audio signal processor 82 and a speaker 83. The audio signal processor 82 is coupled to the microphone 80 by a wireless or hardwired interface.

The microphone 80 is disposed for detecting the breathing of the patient while the patient is wearing the facial cushion and in the prone position. In one embodiment, the microphone 80 is disposed in the video camera 11. In an alternative embodiment, the microphone 80 is disposed adjacent the platform 28, which is shown in FIG. 1. The audio signal processor 82 processes the signals received from the microphone 80. The speaker 83 is coupled to the audio signal processor 82 to reproduce the sounds of the patient's breathing.

The speaker 83 is located so that the sounds of the patient's breathing can be heard by medical personnel having the responsibility of monitoring the patient's breathing during the medical procedure. The speaker 83 may be included in a headset or contained in a casing that is disposed on a table or the like; or the speaker casing is configured for being attached to a person or some object, such as a wall or some apparatus, such as an operating table. The speaker 83 is coupled to the audio signal processor 82 by a wireless or hardwired interface.

An alternative embodiment of the audio system also includes an audio recorder 84, which is coupled to the audio signal processor 82 for making an audio record of the patient's breathing during a medical procedure while the patient is wearing the facial cushion and in the prone position. The audio record may be used to corroborate the video recording made by the video recorder 38.

In an embodiment in which the microphone 80 is included in the video camera 11, the audio signal processor 82 is included in the circuit box 15 of the video camera, the speaker 83 is included with the video monitor 12 in a television monitor and/or the audio recorder 84 is included in the video recorder 38.

In an embodiment that includes the computer 37 and the alerting device 40, the speaker 83 and the alerting device 40 can be integrated to provide an audible alert when the computer 37 detects that the predetermined threshold is exceeded, as shown at 48 in FIG. 6.

In further alternative embodiments (not shown), (a) the video camera lens is disposed for viewing images that are reflected off of a mirror or off of two mirrors; and/or (b) the video camera lens is mounted inside the cushion support casing or inside the facial cushion; and/or (c) the video camera lens is mounted on adjustment screws to travel with an extension to provide an optimum focal point; and/or (d) the video camera or the video camera lens is secured to a mirrored surface for viewing the face of a patient from beneath the face of a patient wearing the cushion and in a prone position.

The self-supporting facial cushion may have a different configuration than either the facial cushion 10 shown in FIGS. 1, 2, 3 and 4 or the facial cushion 50 shown in FIGS. 7 and 8.

In still other embodiments the various aspects of the different embodiments described herein are combined with one another to the extent that they are not incompatible with each other.

The benefits specifically stated herein do not necessarily apply to every conceivable embodiment of the present invention. Further, such stated benefits of the present invention are only examples and should not be construed as the only benefits of the present invention.

While the above description contains many specificities, these should not be construed as limitations on the scope of the present invention, but rather as examples of the preferred embodiments described herein. Other variations are possible and the scope of the present invention should be determined not by the embodiments described herein but rather by the claims and their legal equivalents.

The invention claimed is:

1. An apparatus that allows at least one feature of a patient's face to be observed while the patient is in a prone position, comprising:
   a facial cushion for providing cranial support for a patient in a prone position during a medical procedure, wherein the cushion has at least one frontal aperture that is dimensioned so that at least one facial feature of the patient wearing the facial cushion and in a prone position is visible through the at least one aperture from beneath the patient;
   a video camera having a lens for providing video signals representing images of the at least one facial feature that is visible through the at least one frontal aperture when the cushion is supporting the head of the patient in a prone position;
   wherein a portion of the cushion defines a tunnel through which at least the lens of the video camera can be inserted longitudinally with respect to the patient's face from outside the cushion to a position that is beneath the patient's face when a patient wearing the facial cushion is in the prone position;
   a tray that is dimensioned for carrying the video camera through the tunnel in the cushion, wherein the tray includes a compartment that is dimensioned for fitting a cartridge that contains the video camera within the compartment so that the camera cartridge does not slide and change position with respect to the tray when the camera cartridge is placed in the compartment of the tray; and
   a receptacle placed in relation to the cushion for receiving the camera beneath the at least one frontal aperture of the cushion when the cushion is disposed for providing said cranial support, said receptacle being adapted for enabling the lens of the camera to be disposed in a predetermined position beneath the face of the prone patient wearing the cushion when the tray is inserted through the tunnel in the cushion, wherein the camera is in a cartridge that includes a guide for engaging the receptacle to facilitate placement of the camera in said predetermined position.

2. The apparatus according to claim 1, wherein the tray includes a bar having a lateral dimension that is wider than the width of the tunnel, with the bar being disposed on the tray for limiting the distance of movement of the tray through the tunnel so that in accordance with the length of the tray and the configuration of the cushion, the lens of the video camera within the tray can be located in a predetermined stationary position, beneath the face of the patient wearing the facial cushion.

3. The apparatus according to claim 1, wherein the tray includes a compartment that is dimensioned by moving a slideable interior wall for fitting the video camera within the compartment so that the video camera does not slide and change position with respect to the tray when the video camera is placed in the compartment of the tray.

4. The apparatus according to claim 1, wherein the bottom of the tray includes a plurality of holes for draining fluid from the tray when fluid collects within the tray during the course of a surgical procedure.

5. An apparatus that allows at least one feature of a patient's face to be observed while the patient is in a prone position, comprising:
   a facial cushion for providing cranial support for the patient in a prone position during a medical procedure, wherein the cushion has at least one frontal aperture that is dimensioned so that at least one facial feature of the patient wearing the facial cushion and in a prone position is visible through the at least one aperture from beneath the patient; and
   a video camera having a lens for providing video signals representing images of the at least one facial feature that is visible through the at least one frontal aperture when the cushion is self supported and supporting the head of the patient in a prone position;
   wherein a portion of the cushion that contacts a supporting surface when the cushion is providing said cranial support defines a tunnel through which at least the lens of the video camera can be inserted from outside the cushion to a position that is beneath the patient's face when the patient wearing the facial cushion is in the prone position;
   said apparatus further comprising:
   a tray that is dimensioned for carrying the video camera through the tunnel in the cushion; and
   a receptacle placed in relation to the cushion for receiving the tray beneath the at least one frontal aperture of the cushion when the cushion is disposed for providing said cranial support, said receptacle being adapted for enabling the lens of the camera to be disposed in a predetermined position beneath the face of the prone patient wearing the cushion when the tray is inserted through the tunnel in the cushion.

6. The apparatus according to claim 5, wherein the camera is in a cartridge that includes a guide for engaging the receptacle to facilitate placement of the camera in said predetermined position when the tray is inserted through the tunnel in the cushion.

7. A method of allowing at lean one feature of the patient's face to be observed while the patient is in a prone position, comprising the steps of:
   (a) using a facial cushion to provide cranial support for the patient in a prone position during a medical procedure, wherein the cushion has at least one frontal aperture that is dimensioned so that at least one facial feature of a patient wearing the facial cushion and in a prone position is visible through the at least one aperture from beneath the patient;
   (b) using a video camera having a lens to provide video signals representing images of the at least one facial feature that is visible through the at least one frontal aperture when the cushion is supporting the head of the patient in a prone position;
   wherein a portion of the cushion that contacts a supporting surface when the cushion is providing said cranial support defines a tunnel, through which at least the lens of the video camera can be inserted from outside the cushion;
   (c) inserting the lens of the video camera through the tunnel to a position that is beneath the patient's face when the patient wearing the facial cushion is in the prone position; and
   (d) inserting the video camera through the tunnel on a tray that is dimensioned for carrying the video camera;
   (e) placing a receptacle in relation to the cushion for receiving the tray beneath the at least one frontal aperture of the cushion when the cushion is providing said cranial support, said receptacle being adapted for enabling the lens of the camera to be disposed in a predetermined position that is beneath the face of the said prone patient wearing the cushion when the tray is inserted through the tunnel in the cushion.

8. A method according to claim 7, further comprising the step of:
   (f) when the camera is in a cartridge that includes a guide for engaging the receptacle, facilitating placement of the camera in said predetermined position when the tray is inserted through the tunnel by engaging the receptacle with the guide.

9. A method according to claim 7, further including the step of:
   (f) using the tray includes a bar having a lateral dimension that is wider than the width of the tunnel, with the bar being disposed on the tray for limiting the distance of movement of the tray through the tunnel so that in accordance with the length of the tray and the configuration of the cushion, the lens of the video camera within the tray can be located in a predetermined stationary position beneath the face of the patient wearing the facial cushion.

10. A method according to claim 7, further including the step of:
   (f) using the tray that includes a compartment that is dimensioned for fitting a cartridge that contains the video camera within the compartment so that the camera cartridge does not slide and change position with respect to the tray when the camera cartridge is placed in the compartment of the tray.

\* \* \* \* \*

UNITED STATES PATENT AND TRADEMARK OFFICE
CERTIFICATE OF CORRECTION

PATENT NO.       : 8,269,825 B1
APPLICATION NO.  : 12/506809
DATED            : September 18, 2012
INVENTOR(S)      : An Binh Vu et al.

Page 1 of 1

It is certified that error appears in the above-identified patent and that said Letters Patent is hereby corrected as shown below:

Column 9, line 9, "lean" should be --least--.

Signed and Sealed this
Twelfth Day of February, 2013

Teresa Stanek Rea
*Acting Director of the United States Patent and Trademark Office*